(12) United States Patent
Hudnall

(10) Patent No.: US 7,599,739 B2
(45) Date of Patent: Oct. 6, 2009

(54) MULTI-CHAMBER TIMING FOR PREMATURE CARDIAC PACING

(75) Inventor: John Harrison Hudnall, Franklin, TN (US)

(73) Assignee: Medtronic, Inc., Minneapolis, MN (US)

( * ) Notice: Subject to any disclaimer, the term of this patent is extended or adjusted under 35 U.S.C. 154(b) by 534 days.

(21) Appl. No.: 11/322,856

(22) Filed: Dec. 30, 2005

(65) Prior Publication Data

US 2007/0156192 A1   Jul. 5, 2007

(51) Int. Cl.
*A61N 1/362* (2006.01)
(52) U.S. Cl. .............................. 607/9; 607/2
(58) Field of Classification Search ............ 607/9, 607/10, 25, 27, 116, 119, 123
See application file for complete search history.

(56) References Cited

U.S. PATENT DOCUMENTS

| 5,213,098 A | 5/1993 | Bennett et al. | |
| 6,496,730 B1 * | 12/2002 | Kleckner et al. | 607/9 |
| 7,289,850 B2 | 10/2007 | Burnes | |
| 2004/0220631 A1 * | 11/2004 | Burnes et al. | 607/9 |
| 2004/0220636 A1 * | 11/2004 | Burnes | 607/17 |
| 2004/0220640 A1 | 11/2004 | Burnes | |
| 2005/0090872 A1 | 4/2005 | Deno et al. | |
| 2006/0173498 A1 * | 8/2006 | Banville et al. | 607/5 |
| 2006/0247698 A1 * | 11/2006 | Burnes et al. | 607/9 |

FOREIGN PATENT DOCUMENTS

WO   WO2006115890 A   11/2006

* cited by examiner

*Primary Examiner*—Carl H Layno
*Assistant Examiner*—Jennifer Stewart
(74) *Attorney, Agent, or Firm*—Stephen W. Bauer

(57) ABSTRACT

A pacing control is used in multi-chamber cardiac potentiation therapy to provide a first premature pacing pulse to a first chamber based on a previous event sensed in the first chamber, and to provide a second premature pacing pulse to a second chamber based on a previous event sensed in the second chamber.

7 Claims, 3 Drawing Sheets

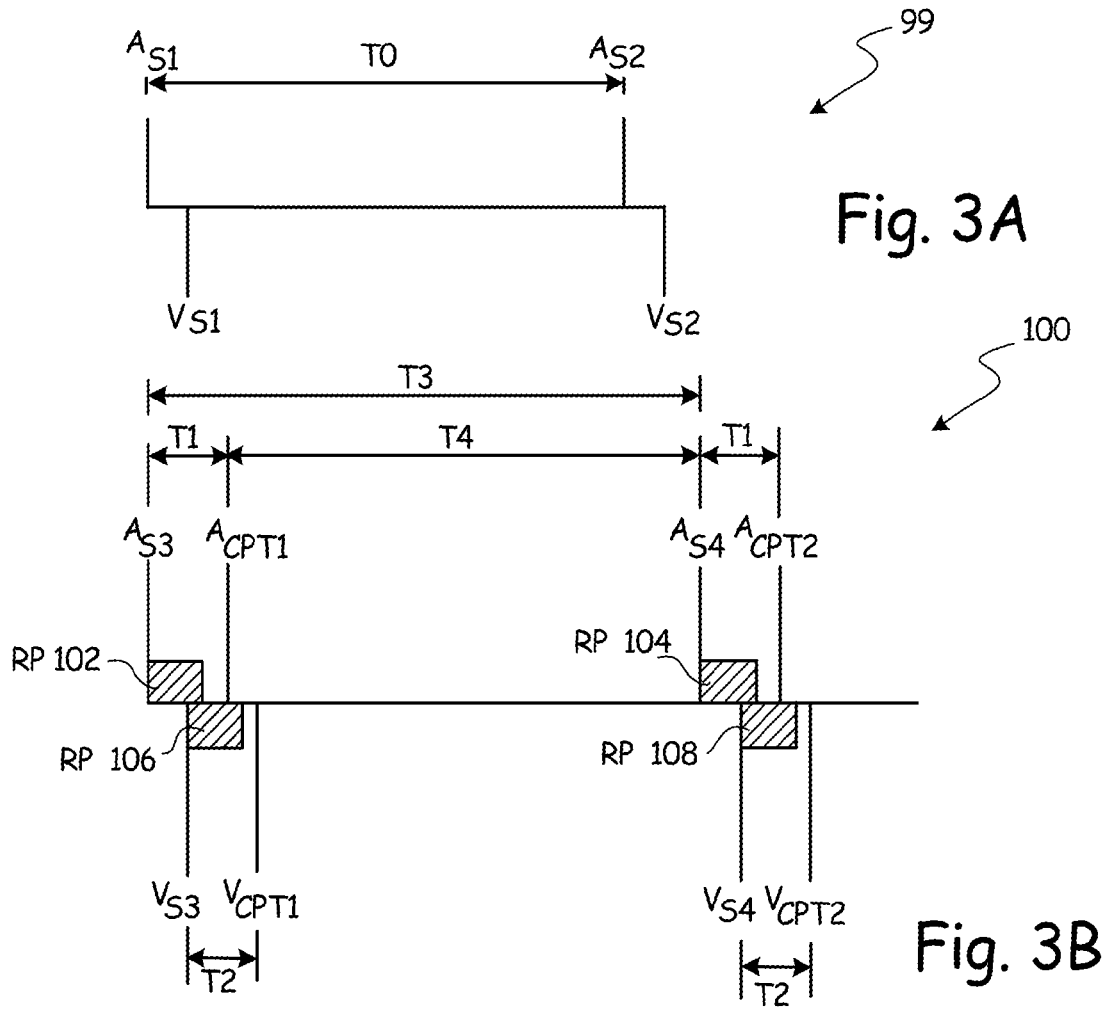
Fig. 3A
Fig. 3B
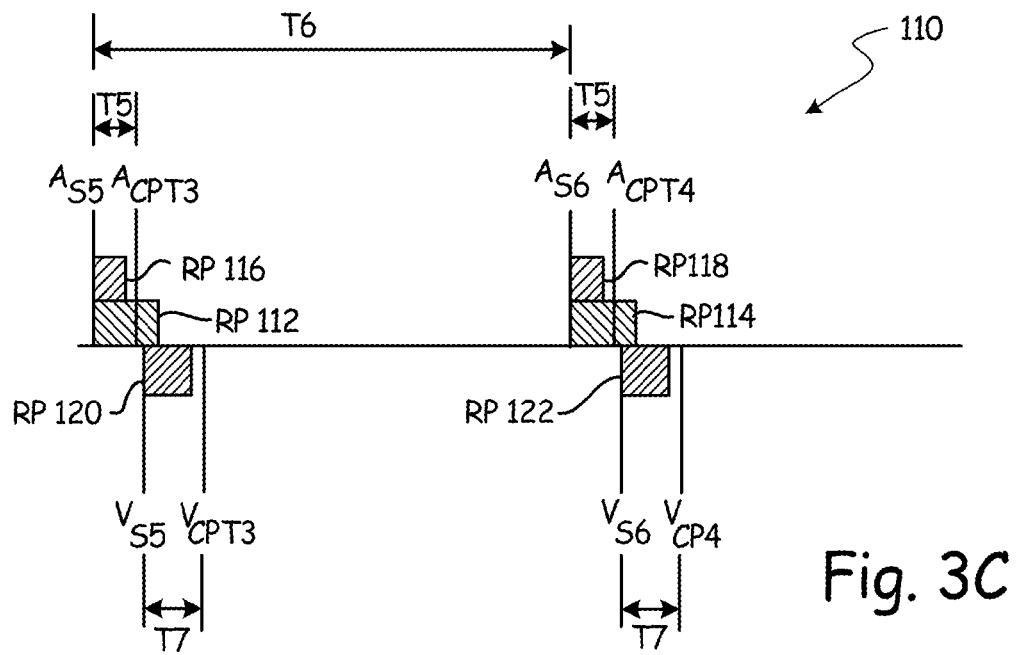
Fig. 3C

MULTI-CHAMBER TIMING FOR PREMATURE CARDIAC PACING

BACKGROUND OF THE INVENTION

The present invention relates generally to the field of cardiac pacing systems, and more particularly to a cardiac pacing device having pacing control for providing multi-chamber post extrasystolic potentiation (PESP) therapy.

Modern cardiac pacing devices and systems, such as implantable pacemakers and cardioverter-defibrillators, are capable of providing PESP therapy to one or more chambers of the heart. A device providing PESP therapy prematurely excites the atria and/or the ventricles, causing a premature contraction. If timed properly, the premature contraction provides an effect that increases contractility, i.e., the ability of the myocardium to contract and relax. An increase in contractility leads to an increase in stroke volume (i.e., the amount of blood ejected from the ventricles per heartbeat). Thus, an increase in contractility is desirable, particularly in patients suffering from heart failure (HF).

In typical cardiac pacing devices and systems providing PESP therapy timing of delivery of both the premature atrial pulse and the premature ventricular pulse is based on a sensed or pulsed ventricular event.

BRIEF SUMMARY OF THE INVENTION

The present invention provides pacing control for use in a multi-chamber cardiac pacing system that provides PESP therapy. The system provides premature cardiac pacing to a particular chamber based on sensed events within that respective chamber.

BRIEF DESCRIPTION OF THE DRAWINGS

FIG. 3A is timing diagram illustrating baseline sinus rhythm in the absence of PESP therapy.

FIGS. 3B and 3C are timing diagrams illustrating delivery of PESP therapy in accordance with the prevent invention for use in the implantable medical device.

DETAILED DESCRIPTION

The present invention provides multi-chamber timing for premature cardiac paces delivered as part of a PESP therapy. Premature cardiac paces delivered to a particular chamber are delivered based on sensed events within that chamber. For instance, a premature pulse delivered to the right atrium is based on a sensed atrial event within the right atrium. Providing premature atrial and ventricular premature pulses based on sensed or pulsed events detected in the respective chambers results in potentiation of each chamber being maximized. Furthermore, providing premature atrial paces based on atrial sensed or paced events provides better control of the mechanical rate of the heart.

Figure 1:
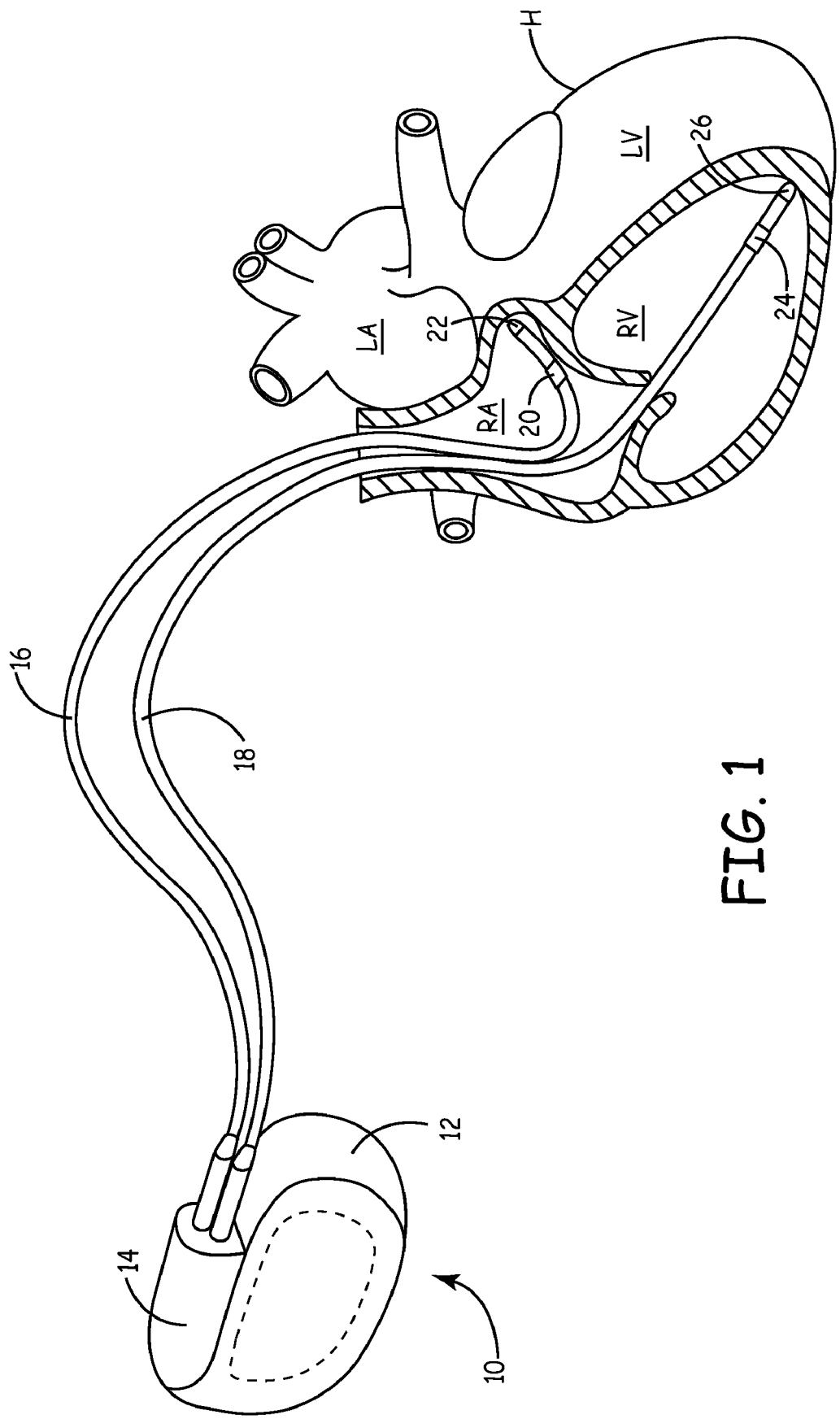
FIG. 1 is a diagram of an implantable medical device and lead set of a type in which the present invention may be practiced.

FIG. 1 is a diagram of implantable medical device (IMD) 10 capable of providing pacing therapy to heart H in accordance with the present invention. IMD 10 is presented herein as one embodiment of an intracardiac pacing system that embodies the pacing control of the present invention. However, the pacing control of the present invention may be adapted for use with any multiple chamber pacing or defibrillation system that allows for delivery of PESP therapy.

In the embodiment illustrated in FIG. 1, IMD 10 includes hermetically-sealed housing 12, header 14, right atrial (RA) lead 16, and right ventricular (RV) lead 18. IMD 10 further includes circuitry and a power source, which are located within housing 12, for controlling the operation of IMD 10. The circuitry, which includes the pacing control of the present invention, communicates with leads 16 and 18 through electrical connectors within header 14. Leads 16 and 18 extend from header 14 to right atrium RA and right ventricle RV, respectively, of heart H. Leads 16 and 18 carry one or more sensors/electrodes for sensing electrical signals attendant to the depolarization and repolarization of heart H, and further for providing pacing pulses for causing depolarization of cardiac tissue in the vicinity of the distal ends thereof. As shown in FIG. 1, atrial ring and tip electrodes 20 and 22 are disposed at the distal end of RA lead 16 and are located in right atrium RA. Similarly, ventricular ring and tip electrodes 24 and 26 are disposed at the distal end of RV lead 18 and are located in right ventricle RV.

Figure 2:
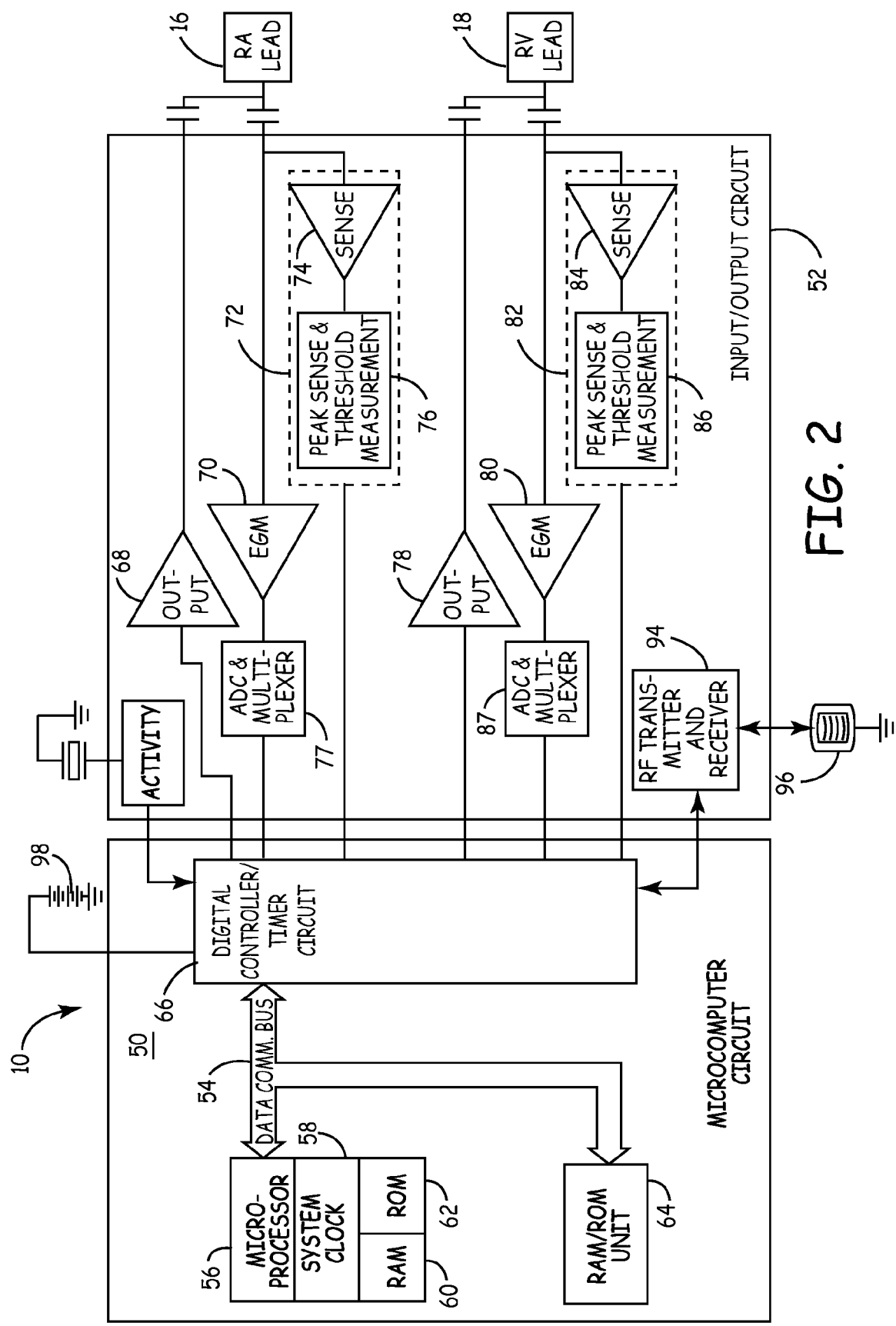
FIG. 2 is functional block diagram of the circuitry of the implantable medical device of FIG. 1.

FIG. 2 is a functional block diagram of the circuitry located within IMD 10. This block diagram is intended to be merely an example and corresponds only to a general functional organization of most presently available IMDs. The circuitry generally includes microcomputer circuit 50, input/output circuit 52, and data communications bus 54.

Microcomputer circuit 50 includes microprocessor 56, system clock 58, on-board RAM memory 60, on-board ROM memory 62, off-board RAM/ROM memory 64, and digital controller/timer circuit 66 connected to microprocessor 56 and off-board RAM/ROM memory 64 via data communications bus 54. Microcomputer circuit 50 communicates with input/output circuit 52 to monitor electrical activity in heart H as well as to deliver appropriately-timed pulses to the various electrodes. Digital controller/timer circuit 66 includes digital timers and counters used to determine time between successive depolarizations in the atria and ventricles, as well as to provide various refractory, blanking, and other timing windows used to determine delivery of paced pulses to the atria and ventricles. Digital controller/timer circuit 66 receives sensed activity signals and causes pacing pulses to be delivered via connections to leads 16 and 18.

RA lead 16 is connected to digital controller/timer circuit 66 via output pulse generator 68, electrogram (EGM) amplifier 70, and sensing circuitry 72, which includes sense amplifier 74 and peak sense and threshold measurement circuitry 76. Sense amplifier 74 amplifies electrical cardiac signals sensed by RA lead 16 and provides an amplified signal to peak sense and threshold measurement circuitry 76, which in turn provides an indication of sensed cardiac events and measured sense amplifier threshold voltages to digital controller/timer circuit 66. Electrical signals sensed by RA lead 16 provide microcomputer 50 with information regarding depolarizations in right atrium RA. Signals received by RA lead 16 are also provided to EGM amplifier 70 and are converted into digital values by analog-to-digital converter (ADC) and multiplexer 77. The output of ADC and multiplexer 77 provides a digitized version of the EGM signal, which IMD 10 may transmit when interrogated by an external programmer (not shown) to transmit a representation of a cardiac EGM. Under the control of microcomputer circuit 50 and digital controller/timer circuit 66, output pulse generator 68 provides pacing pulses to RA lead 16.

In a similar fashion, RV lead 18 is also connected to digital controller/timer circuit 66 via output pulse generator 78, EGM amplifier 80, and sensing circuitry 82, which includes sense amplifier 84 and peak sense and threshold measurement circuitry 86. Sense amplifier 84 amplifies electrical cardiac signals sensed by RV lead 18 and provides an amplified signal to peak sense and threshold measurement circuitry 86, which in turn provides an indication of sensed cardiac events and measured sense amplifier threshold voltages to digital controller/timer circuit 66. Electrical signals sensed by RV lead 18 provide microcomputer 50 with information regarding depolarizations in right ventricle RV. Signals received by RV lead 18 are also provided to EGM amplifier 80 and are converted to a digital value by ADC and multiplexer 87. The output of the ADC and multiplexer 87 provides a digitized version of the EGM signal, which IMD 10 may transmit to the external programmer when interrogated. Under the control of microcomputer circuit 50 and digital controller/timer circuit 66, output pulse generator 78 provides pacing pulses to RV lead 18.

IMD 10 also includes RF transmitter and receiver 94 and antenna 96, which allows IMD 10 to be programmed by means of an external programming unit (not shown). Power is supplied to all systems of IMD 10 by power supply 98.

FIG. 3A is a timing diagram illustrating a baseline or intrinsic sinus rhythm of heart H if no PESP therapy is delivered. Timing diagram 99 includes sensed atrial events $A_{S1}$ and $A_{S2}$ and sensed ventricular events $V_{S1}$ and $V_{S2}$. Sensed atrial events $A_{S1}$ and $A_{S2}$ are generically used to describe atrial activity, but may be the result of paced pulses provided by IMD 10 to right atrium RA. Likewise, sensed ventricular events $V_{S1}$ and $V_{S2}$ are generically used to describe ventricular activity, but may be the result of paced pulses provided by IMD 10 to right ventricle RV. These terms are also used to describe atrial and ventricular events in FIGS. 3B and 3C.

The time between successive sensed atrial events ($A_{S1}$ and $A_{S2}$) is typically controlled by a sino-atrial (SA) node of heart H. The SA node automatically causes a depolarization within the SA node that is conducted through right atrium RA at time T0 following a previous SA node depolarization. If SA node does not depolarize automatically, a paced atrial pulse can be provided by IMD 10 at a programmed lower rate interval (LRI). The mechanical rate of heart H, commonly describe as the heart rate, is defined by the time T0 between successive sensed atrial events $A_{S1}$ and $A_{S2}$, and in turn the time (approximately equal to time T0) between successive sensed ventricular events $V_{S1}$ and $V_{S2}$. For instance, in one embodiment the SA node automatically maintains time interval T0 at approximately 800 milliseconds (ms), which results in a mechanical rate of heart H of approximately 75 beats per minute (bpm) in heart H. The intrinsic sinus rhythm shown in FIG. 3A provides a reference point with which to discuss the effects of PESP delivered by IMD 10 in FIGS. 3B and 3C.

FIGS. 3B and 3C are timing diagrams illustrating delivery of PESP according to the present invention. Delivery of PESP requires IMD 10 to deliver premature pacing pulses $A_{PESP}$ or $V_{PESP}$ ($A_{PESP}$ and $V_{PESP}$ denote pulses delivered as part of PESP therapy) following a sensed or paced event. Pacing pulses are delivered by IMD 10 via output pulse generators 68 and 78 to RA lead 16 and RV lead 18, respectively. Timing diagram 100 includes sensed atrial events $A_{S3}$ and $A_{S4}$, premature atrial pulses $A_{PESP1}$ and $A_{PESP2}$, ventricular sensed events $V_{S3}$ and $V_{S4}$, and premature ventricular pulses $V_{PESP1}$ and $V_{PESP2}$. Atrial refractory period (RP) following sensed atrial events $A_{S3}$ and $A_{S4}$ is shown by shaded regions 102 and 104, respectively. Ventricular refractory period (RP) following sensed ventricular events $V_{S3}$ and $V_{S4}$ is shown by shaded regions 106 and 108, respectively.

IMD 10 times delivery of premature atrial pulse $A_{PESP1}$ based on sensed atrial event $A_{S3}$. Premature atrial pulse $A_{PESP1}$ must be delivered outside of atrial RP 102, such that premature atrial pulse $A_{PESP1}$ is able to cause a depolarization, and therefore, contraction of right atrium RA. Furthermore, by providing premature atrial pulse $A_{PESP1}$ close in time with sensed atrial event $A_{S3}$, the potentiation provided to right atrium RA is maximized. As shown in FIG. 3B, premature atrial pulse $A_{PESP1}$ is delivered at a time interval T1 following sensed atrial event $A_{S3}$. Premature atrial pulse $A_{PESP2}$ is also delivered outside of atrial RP 104 following sensed atrial event $A_{S4}$.

IMD 10 times delivery of premature ventricular pulse $V_{PESP1}$ based on sensed ventricular event $V_{S3}$. Premature ventricular pulse $V_{PESP1}$ must also be delivered outside of ventricular RP 106, such that premature ventricular pulse $V_{PESP1}$ is able to cause a depolarization, and therefore, contraction of right ventricular RV. Providing premature ventricular pulse $V_{PESP1}$ close in time with sensed ventricular event $V_{S3}$ maximizes the potentiation benefits to right ventricle RV. As shown in FIG. 3B, premature ventricular pulse $V_{PESP1}$ is delivered at a time interval T2 following sensed ventricular event $V_{S3}$. Time interval T2 may or may not be equal to time interval T1, depending on the refractory periods associated with right atrium RA and right ventricle RV.

The mechanical rate of heart H, as described above, is a function of the time T3 between successive sensed atrial events $A_{S3}$ and $A_{S4}$, and in turn the time (approximately equal to time T3) between successive sensed ventricular events $V_{S3}$ and $V_{S4}$. Premature atrial and ventricular paced pulses $A_{PESP1}$ and $V_{PESP1}$ do not cause either right atrium RA or right ventricle RV to expel blood from the respective chambers, and thus do not directly effect the mechanical rate of heart H. However, premature atrial pulses can potentially decrease the mechanical rate of heart H by depolarizing and in effect resetting the SA node of heart H. As discussed above, the time between successive sensed atrial events is typically controlled by the SA node of heart H, which automatically causes a depolarization of the atrium at a defined time interval (i.e., time interval T0 as shown in FIG. 3A) following a previous depolarization of the SA node.

In FIG. 3B, the time interval defined by the SA node is shown as time interval T4, which is approximately equal to time interval T0 as shown in FIG. 3A. Delivering premature atrial pulse $A_{PESP1}$ may have the effect of depolarizing and resetting the SA node, resulting in sensed atrial pulse $A_{S4}$ being delivered or sensed at a time interval T3 (where T3=T1+T4) following sensed atrial event $A_{S3}$. This has the effect of extending the time between sensed atrial events $A_{S3}$ and $A_{S4}$ with respect to the intrinsic sinus rhythm shown in FIG. 3A, resulting in a decrease in the mechanical rate or heartbeat of a patient. By minimizing time period T1 between sensed atrial event $A_{S3}$ and premature atrial pace $A_{PESP1}$, while maintaining premature atrial pace $A_{PESP1}$ outside of atrial refractory period 102, time interval T3 is also minimized and the mechanical rate of heart H is maintained as close as possible to the intrinsic sinus rhythm. Thus, by basing premature atrial paces (i.e., $A_{PESP1}$ and $A_{PESP2}$) on sensed atrial events (i.e., $A_{S3}$ and $A_{S4}$, respectively) and corresponding atrial refractory periods (i.e., atrial RP 102 and 104, respectively), IMD 10 provides potentiation to the atrium while maintaining the mechanical rate of heart H at the highest rate possible.

Timing diagram 110 shown in FIG. 3B illustrates delivery of PESP therapy without directly affecting the mechanical rate or heartbeat of heart H. Timing diagram 110 includes sensed atrial events $A_{S5}$ and $A_{S6}$, premature atrial pulses $A_{PESP3}$ and $A_{PESP4}$, ventricular sensed events $V_{S5}$ and $V_{S6}$, and premature ventricular pulses $V_{PESP3}$ and $V_{PESP4}$. Atrial refractory period (RP) following sensed atrial events $A_{S5}$ and $A_{S6}$ is divided into SA node RP 112 and 114, respectively, and non-nodal atrial RP 116 and 118, respectively.

In some patients, the SA node RP (as shown by RP 112 and 114) is longer than the non-nodal atrial RP (as shown by 116 and 118), as shown in FIG. 3B. If this situation exists, then IMD 10 delivers premature atrial pulse $A_{PESP3}$ outside of non-nodal atrial RP 116, but within SA node RP 112, at time interval T5 following atrial sensed event $A_{S5}$. Delivering premature atrial pulse $A_{PESP3}$ within this window provides the desired atrial potentiation effects in right atrium RA without depolarizing and therefore resetting the SA node. The benefit of delivering premature atrial pulse $A_{PESP3}$ during the SA node RP 112, is the SA node generates sensed atrial event $A_{S6}$ at time period T6 following sensed atrial event $A_{S5}$, which is approximately equal to the intrinsic sinus rhythm illustrated by time interval T0 in FIG. 3A. If time interval T6 is approximately equal to time period T0, then the mechanical rate of heart H is maintained at a rate determined by the SA node.

This is in contrast with the timing diagram shown in FIG. 3B, in which SA node was reset by premature atrial pulse $A_{PESP1}$, resulting in an extended time interval between sensed atrial event $A_{S3}$ and $A_{S4}$. The delivery of PESP therapy as shown in FIG. 3C maintains the intrinsic sinus rhythm interval between successive sensed atrial events (and thus the mechanical rate defined by the intrinsic sinus rhythm), while providing potentiation benefits to both right atrium RA and right ventricle RV. If PESP therapy can be delivered to a particular patient in this manner, without directly lowering the mechanical rate of heart H, then PESP therapy may be delivered for long periods of time without adverse effects caused by a reduction in the mechanical rate of heart H.

In FIG. 3C, premature ventricular pulses $V_{PESP3}$ and $V_{PESP4}$ are delivered at time period T7 following sensed ventricular events $V_{S5}$ and $V_{S6}$, outside of ventricular RPs 120 and 122, providing maximum potentiation benefits to right ventricle RV.

Therefore, FIG. 3C illustrates PESP therapy in which IMD 10 times delivery of a premature atrial pulse within a window defined by the sino-atrial refractory period and the non-nodal refractory period. This provides potentiation benefits to the atrium and allows the sino-atrial node to maintain direct control of the mechanical heart rate at a rate approximately equal to the intrinsic rhythm rate (i.e., time interval T6≈time interval T0).

In the timing diagrams shown in FIGS. 3B and 3C, in order to deliver properly timed premature atrial and ventricular pulses, IMD 10 must determine the length of refractory periods following atrial and ventricular sensed events. In one embodiment, IMD 10 delivers a premature atrial pulse at a first initial time interval following a sensed atrial event, and delivers premature ventricular pulse at a second initial time interval following a sensed ventricular event. IMD 10 determines whether either the premature atrial pulse or the premature ventricular pulse caused a depolarization and therefore contraction of either the right atrium or right ventricle. For example, if IMD 10 determines that the premature atrial pulse did not cause a depolarization or contraction in the atrium, then IMD 10 lengthens the first initial time interval and delivers another premature atrial pulse following the next atrial sensed event. This process is continued until a proper timing interval is determined (i.e., outside of the atrial refractory period but close in time with the atrial sensed event). The same process is performed with respect to the premature ventricular pulses delivered by IMD 10.

In order to determine whether a premature atrial pulse is properly timed within the window defined by the SA node RP and the non-nodal RP (as shown in FIG. 3C), IMD 10 provides a premature atrial pace and either shortens or lengthens the time interval associated with the premature atrial pace based on the sensed response. For example, IMD 10 delivers a first premature atrial pace following a first sensed atrial event, resulting in a depolarization of the atrium and a time interval between the first sensed atrial event and a second sensed atrial event greater than the intrinsic sinus rate. Based on this feedback, IMD 10 determines that the first premature atrial pace was delivered outside of both the SA node refractory period and the non-nodal refractory period. In response, IMD 10 shortens the interval between the second or subsequent sensed atrial event and a second premature atrial pace. If the second premature atrial pace results in a depolarization of the atrium, along with a time interval between the second sensed atrial event and the third sensed atrial event approximately equal to the intrinsic rhythm rate of heart H, then IMD 10 determines that the second premature atrial pace was delivered within the window defined by the SA node refractory period and the non-nodal refractory period. Subsequent premature atrial paces will be delivered at the same interval.

As described above, IMD 10 provides PESP therapy to the right atrium RA based on atrial sensed events and provides PESP therapy to the right ventricle RV based on ventricular sensed events. Providing PESP therapy in this manner provides maximum potentiation benefit to both the right atrium RA and right ventricle RV. Furthermore, providing PESP therapy in this manner minimizes decreases in the mechanical rate of heart H. In other embodiments, PESP therapy is implemented in multi-chamber IMD to allow the IMD to deliver premature pacing pulses to the left atrium LA and left ventricle LV, based on sensed activity in the left atrium LA and left ventricle LV, respectively.

The invention claimed is:

1. A method of providing cardiac potentiation therapy, the method comprising:
   sensing an atrial depolarization;
   delivering a premature atrial pace based on the sensed atrial depolarization at a first time interval following the sensed atrial depolarization;
   sensing a ventricular depolarization;
   delivering a premature ventricular pace based on the sensed ventricular depolarization at a second time interval following the sensed ventricular depolarization; and
   selecting the first time interval to be greater than a non-nodal atrial refractory period caused by the sensed atrial depolarization and less than a sino-atrial node refractory period caused by the sensed atrial depolarization to prevent the sino-atrial node from being depolarized by the premature atrial pace.

2. A method according to claim 1, further including:
   determining whether the premature atrial pace delivered at the first time interval depolarized the atrium; and
   increasing the first time interval and delivering a subsequent premature atrial pace following a subsequent sensed atrial depolarization at the increased time interval if the premature atrial pace did not depolarize the atrium.

3. A method according to claim 1, wherein delivering the premature atrial pace includes:
   determining whether the premature atrial pace delivered at the first time interval depolarized the sino-atrial node; and
   decreasing the first time interval and delivering a subsequent premature atrial pace following a subsequent sensed atrial depolarization at the decreased time interval if the premature atrial pace did depolarize the sinoatrial node.

4. A method according to claim 1, further including:

selecting the second time interval to be greater than a ventricular refractory period associated with the sensed ventricular depolarization.

5. A method according to claim 4, further including:

determining whether the premature ventricular pace delivered at the second time interval depolarized the ventricle; and increasing the second time interval and delivering a subsequent premature ventricular pace following a subsequent sensed ventricular depolarization at the increased time interval if the premature ventricular pace did not depolarize the ventricle.

6. A method of providing cardiac potentiation therapy (PESP), the method comprising:

sensing an atrial depolarization;

delivering a premature atrial pace based on the sensed atrial depolarization at a first time interval following the sensed atrial depolarization; and selecting the first time interval to be greater than a nonnodal atrial refractory period caused by the sensed atrial depolarization and less than a sino-atrial node refractory period caused by the sensed atrial depolarization to prevent the sino-atrial node from being depolarized by the premature atrial pace.

7. A method according to claim 6, wherein delivering the premature atrial pace includes:

determining whether the premature atrial pace delivered at the first time interval depolarized the sino-atrial node; and decreasing the first time interval and delivering a subsequent premature atrial pace following a subsequent sensed atrial depolarization at the decreased time interval if the premature atrial pace did depolarize the sino-atrial node.

* * * * *

UNITED STATES PATENT AND TRADEMARK OFFICE
CERTIFICATE OF CORRECTION

| | | |
|---|---|---|
| PATENT NO. | : 7,599,739 B2 | Page 1 of 1 |
| APPLICATION NO. | : 11/322856 | |
| DATED | : October 6, 2009 | |
| INVENTOR(S) | : John Harrison Hudnall | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 814 days.

Signed and Sealed this

Twenty-eighth Day of September, 2010

David J. Kappos
*Director of the United States Patent and Trademark Office*